United States Patent
Burrell

(10) Patent No.: US 9,592,418 B2
(45) Date of Patent: Mar. 14, 2017

(54) DYNAMIC STRETCHING, STRENGTHENING AND STABILIZATION DEVICE FOR POSTURAL CORRECTION AND RETRAINING

(71) Applicant: Posture Perfector LLC, Austin, TX (US)

(72) Inventor: Gabriel Luke Burrell, Austin, TX (US)

(73) Assignee: Posture Perfector LLC, Austin, TX (US)

(*) Notice: Subject to any disclaimer, the term of this patent is extended or adjusted under 35 U.S.C. 154(b) by 13 days.

(21) Appl. No.: 14/375,229

(22) PCT Filed: Feb. 8, 2013

(86) PCT No.: PCT/CA2013/000112
§ 371 (c)(1),
(2) Date: Jul. 29, 2014

(87) PCT Pub. No.: WO2013/116934
PCT Pub. Date: Aug. 15, 2013

(65) Prior Publication Data
US 2014/0371039 A1 Dec. 18, 2014

Related U.S. Application Data

(60) Provisional application No. 61/596,636, filed on Feb. 8, 2012.

(51) Int. Cl.
*A63B 21/02* (2006.01)
*A63B 21/055* (2006.01)
(Continued)

(52) U.S. Cl.
CPC .......... *A63B 21/0552* (2013.01); *A61F 5/026* (2013.01); *A63B 21/00043* (2013.01);
(Continued)

(58) Field of Classification Search
CPC ....... A63B 21/00; A63B 21/05; A63B 21/055; A63B 21/0552; A63B 21/0555;
(Continued)

(56) References Cited

U.S. PATENT DOCUMENTS 1,432,013 A * 10/1922 Blake ................. A63B 21/0004
482/124
4,057,246 A * 11/1977 Wilson ............... A63B 21/0552
482/125
(Continued)

FOREIGN PATENT DOCUMENTS

| GB | 2228869 | 9/1990 |
|---|---|---|
| WO | WO 92/21411 | 12/1992 |

(Continued)

OTHER PUBLICATIONS

"Posture Pulley" Posture Pulley Neck Exerciser at Meyer Physical Therapy, MeyerPT, downloaded from the Internet on Oct. 23, 2015, https://www.meyerpt.com/posture-pulley-neck-exerciser, 1 page.
(Continued)

*Primary Examiner* — Stephen Crow
*Assistant Examiner* — Garrett Atkinson
(74) *Attorney, Agent, or Firm* — Kagan Binder, PLLC

(57) ABSTRACT

A dynamic stretching, strengthening and stabilization device is provided for postural correction and retraining. The device has a pair of closed loop resistance tubes and a central harness member which positions the closed loop resistance tubes roughly in the form of a FIG. 8. Each loop of the resistance tube is sized to accommodate the arm and shoulder of the user. The device may be used in a stabilization mode or stretching/strengthening mode, and transitions easily between these modes to correct and retrain the user's posture.

25 Claims, 6 Drawing Sheets

(51) Int. Cl.
*A63B 21/00* (2006.01)
*A61F 5/02* (2006.01)
*A63B 23/12* (2006.01)

(52) U.S. Cl.
CPC .. *A63B 21/00061* (2013.01); *A63B 21/00065* (2013.01); *A63B 21/0555* (2013.01); *A63B 21/4035* (2015.10); *A63B 21/4043* (2015.10); *A63B 23/12* (2013.01); *A63B 23/1209* (2013.01); *A63B 23/1245* (2013.01)

(58) Field of Classification Search
CPC .......... A63B 21/0557; A63B 21/00043; A63B 21/00061; A63B 21/00065; A63B 21/1469; A63B 23/00; A63B 23/12
USPC ................ 482/51, 74, 91, 92, 121–130, 148
See application file for complete search history.

(56) References Cited

U.S. PATENT DOCUMENTS

| | | | | |
|---|---|---|---|---|
| 4,090,706 A | * | 5/1978 | Reda | A63B 21/0004 482/122 |
| 4,540,173 A | * | 9/1985 | Hopkins, Jr. | A63B 21/0552 482/124 |
| 4,852,874 A | * | 8/1989 | Sleichter, III | A63B 21/0004 482/122 |
| 5,199,940 A | * | 4/1993 | Morris | A61F 5/055 128/845 |
| D353,172 S | * | 12/1994 | Gaut | D21/692 |
| 5,514,059 A | * | 5/1996 | Romney | A63B 21/0004 482/121 |
| 5,518,481 A | | 5/1996 | Darkwah | |
| 5,681,248 A | * | 10/1997 | Vani | A63B 21/0004 482/10 |
| 5,860,896 A | * | 1/1999 | Mann | A61F 5/026 482/121 |
| 6,244,998 B1 | * | 6/2001 | Hinds | A63B 21/0004 482/124 |
| 6,659,921 B2 | * | 12/2003 | Vernon | A63B 21/4025 482/114 |
| 7,931,572 B1 | * | 4/2011 | Glauser | A63B 21/0004 482/126 |
| 2002/0187884 A1 | * | 12/2002 | McGrath | A63B 21/0552 482/121 |
| 2005/0043154 A1 | | 2/2005 | Atrizadeh | |
| 2005/0271857 A1 | | 12/2005 | Brody et al. | |
| 2007/0287616 A1 | | 12/2007 | Weaver | |

FOREIGN PATENT DOCUMENTS

| | | |
|---|---|---|
| WO | 2006062423 A1 | 6/2006 |
| WO | WO 2006/062423 | 6/2006 |

OTHER PUBLICATIONS

"Posture Pulley Neck Exerciser", Posture Pulley Neck Exerciser: Physical Therapy Equipment, Supplies & Products—Isokinetics, Inc., downloaded from the Internet on Jan. 12, 2016, http://www.isokineticsinc.com/product/pp_N100, 2 pages.

* cited by examiner

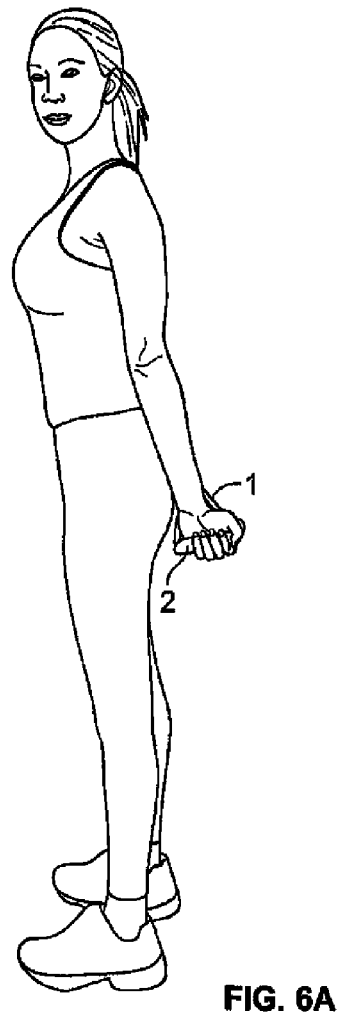
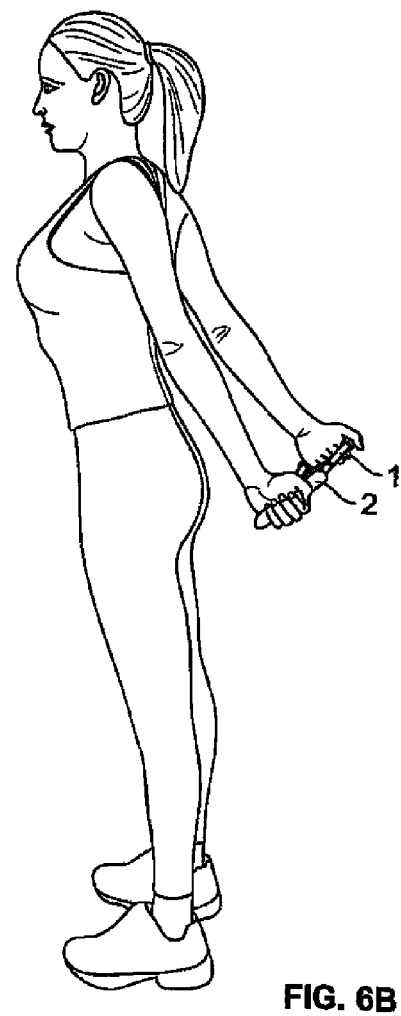
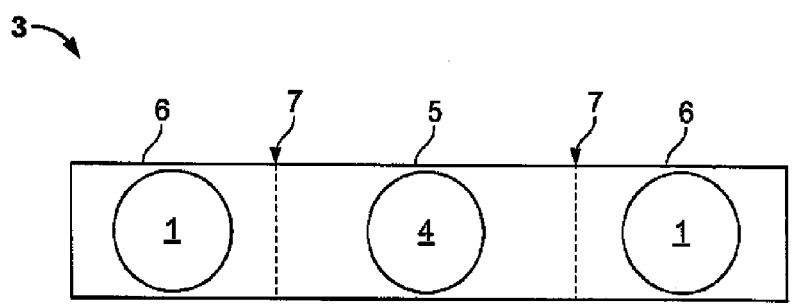
FIG. 6A  FIG. 6B
FIG. 7

DYNAMIC STRETCHING, STRENGTHENING AND STABILIZATION DEVICE FOR POSTURAL CORRECTION AND RETRAINING

RELATED APPLICATION

This application claims the benefit from International Application No. PCT/CA2013/000112, filed Feb. 8, 2013, which in turn claims priority to U.S. Provisional Patent Application having Ser. No. 61/596,636, filed on Feb. 8, 2012, both of which are incorporated herein by reference in their entireties.

FIELD OF INVENTION

This invention generally relates to wearable devices for correction and retraining of a user's posture, and more particularly relates to devices that are dynamic and transition between stretching, strengthening and stabilization modes.

BACKGROUND OF THE INVENTION

When people are at the computer, driving, or sitting for an extended period of time, they begin to develop a forward rolling shoulder complex which is known as "protracted shoulder girdle," or more commonly, "poor posture".

It has been recognized that poor shoulder and upper body posture without effective counter measures such as exercise or stretching induces shortening of the muscle groups in the chest forward segments of the shoulder, and lengthening and weakness in the muscle of the neck, shoulders and upper back. These structural anomalies lead to stiffness, pain, fatigue and other ailments. Good posture, on the other hand, is associated with greater energy, and improved mood and enhanced confidence. Individuals with good posture are also perceived as more authoritative and better looking.

There have been various attempts to provide postural braces for a user to wear to passively correct posture. Such posture systems are not optimal because they cannot be easily put on or removed (they may involve difficult closures, or require difficult reaching to properly position) and may be uncomfortable to wear (overly binding or "creeping," hot, or sweaty). In addition, such devices can be obtrusive and unsightly, which lessens a user's enthusiasm for wearing them (or for wearing them frequently, as may be needed for a consistent effect).

Such devices are also single dimensional (in that they do not serve any purpose other than to passively counteract a user's poor posture). The user does not actively engage with the device, and therefore only experiences some passive relief from or bracing to correct the poor posture, and would not typically achieve a lasting stretching or strengthening of muscles needed to independently maintain good posture. Further, such devices, when unintegrated with a separate exercise protocol for retraining muscles related to poor posture, typically provide minimal results. Such prior art devices also require or enforce lengthy wear-times for postural reinforcement.

Therefore, it can be appreciated that there exists a need for a device which can be used both actively and passively to correct and retrain poor posture.

SUMMARY OF THE INVENTION

According to a first aspect of the invention, a dynamic stretching, strengthening and stabilization device is provided for postural correction and retraining in a user. The device has a central harness member and a pair of closed loop resistance tubes. The central harness member has a middle panel and two side sleeves. Each resistance tube is slidable within a side sleeve of the central harness member. A flexible handle is disposed on each loop and is slidable along the loop. The user can grip the handles and pull in opposing directions to actively engage the resistance tubes in a stretching/strengthening mode. The user can also position each loop over one of the user's arms so that the central harness member is positioned flat against the user's back and the handles are positioned to cushion where the loop engages the user's pectoral or underarm region in a stabilization mode. The loops are sized to fit snugly on the user and provide passive resistance against forward shoulder curvature in the stabilization mode.

The device may further include a rigid anti-torsion member disposed within the middle panel of the central harness member.

The central harness member is preferably of a durable fabric. In certain embodiments, the central harness member may have a slide-resistant surface. Preferably, the central harness member is sized to sit between the user's shoulder blades and avoid creeping upward.

The loops are preferably disposed in the central harness member such that they do not touch or interfere with each other.

Various dimensions are possible, however, in a preferred embodiment, each handle is between about 3 inches to 12 inches in length and each closed loop resistance tube is between about 12 to 36 inches in circumference. For larger or smaller individuals (including children), it will be appreciated that other larger or smaller sizes may be provided (and the device may be custom-fit for particular individuals).

Length (or tension) adjustment may also be provided for the closed loop resistance tubes.

In one embodiment, the device may be packaged with instructions for carrying out stretching or exercising movements in the stretching/strengthening mode.

According to a second aspect of the invention, a method of using a dynamic stretching, strengthening and stabilization device is provided for postural correction and retraining in a user. The device is as set out above. The method comprises the user selectively:
 gripping the handles and pulling in opposing directions to actively engage the resistance tubes in a stretching/strengthening mode; or
 positioning each loop over one of the user's arms so that the central harness member is positioned flat against the user's back and the handles are positioned to cushion where the loop engages the user's pectoral or underarm region in a stabilization mode; the loops being sized to fit snugly on the user and provide passive resistance against forward shoulder curvature in the stabilization mode.

To remove the device from the stabilization mode, the user may further grip the handles, extend the handles outward from the user's body to stretch and elastically enlarge the loops, and remove the loops from the user's arms while the loops are enlarged.

To smoothly transition from the stabilization mode to the stretching/strengthening mode, the user may further grip the handles, extend the handles outward from the user's body to stretch and elastically enlarge the loops, and remove the loops from the user's arms while the loops are enlarged, thereby freeing the device to permit exercising or stretching with the device in front of or behind the user (or above the user's head).

Various movements are possible in the stretching/strengthening mode. In one example, the user may extend the arms outward with the device disposed over the user's head in a fat stretch motion. This may also include leaning to alternate sides while the arms are extended outward. In another example, the user may extend the arms outward with the device disposed behind the user's body in a shoulder stretch motion. In a further example, the user may extend the arms outward with the device disposed in front of the user's body in a first chest stretch motion. In a second chest motion, the user may extend the arms outward with the device disposed behind the user's head.

BRIEF DESCRIPTION OF THE DRAWINGS

FIGS. 6A-6B show an embodiment of a shoulder stretch motion using the device in stretching/strengthening mode.

FIG. 7 is a sectional view of the central harness member 3 showing side sleeves 5 and middle panel 5 with rigid anti-torsion member 4.

DETAILED DESCRIPTION

A device is provided to promote proper posture of a user and correct and retrain poor posture. The device works dynamically—it transitions smoothly between (i) stretching/strengthening and (ii) stabilization (worn) modes. These modes work synergistically to improve the user's posture and to build the user's awareness of posture while strengthening the associated muscle groups that enable good posture.

The device is designed and engineered for both utilization within a pre-defined program of stretching and strengthening exercises that may be typically prescribed as a protocol for correction of protracted shoulder girdle (a term used to describe poor upper body posture); and to be worn post-exercise as a dynamic, non-restrictive, wearable postural retraining device. When being worn according to the protocol, the device continuously exhibits a mild dynamic force on the wearer, effectively training the body to reposition into a bio-mechanically-correct posture via neurological reinforcement against the physical restraint. This allows for a normal range of motion by the wearer, with feedback increasing as the wearer moves further out of their correct bio-mechanical position and decreasing as the wearer moves towards the correct bio-mechanical position.

Combined, the exercise protocol and the neurological reinforcement aspects of the device and use methodology retrain the user, providing them the mobility, muscular strength and cuing within the afflicted muscle groups typical to poor posture to increasingly self-maintain correct postural position.

When used in worn mode, the device stabilizes the shoulder girdle. The muscles in the shoulder and thoracic spine area are stretched and strengthened when the device is used in stretching/strengthening mode.

Figure 3:
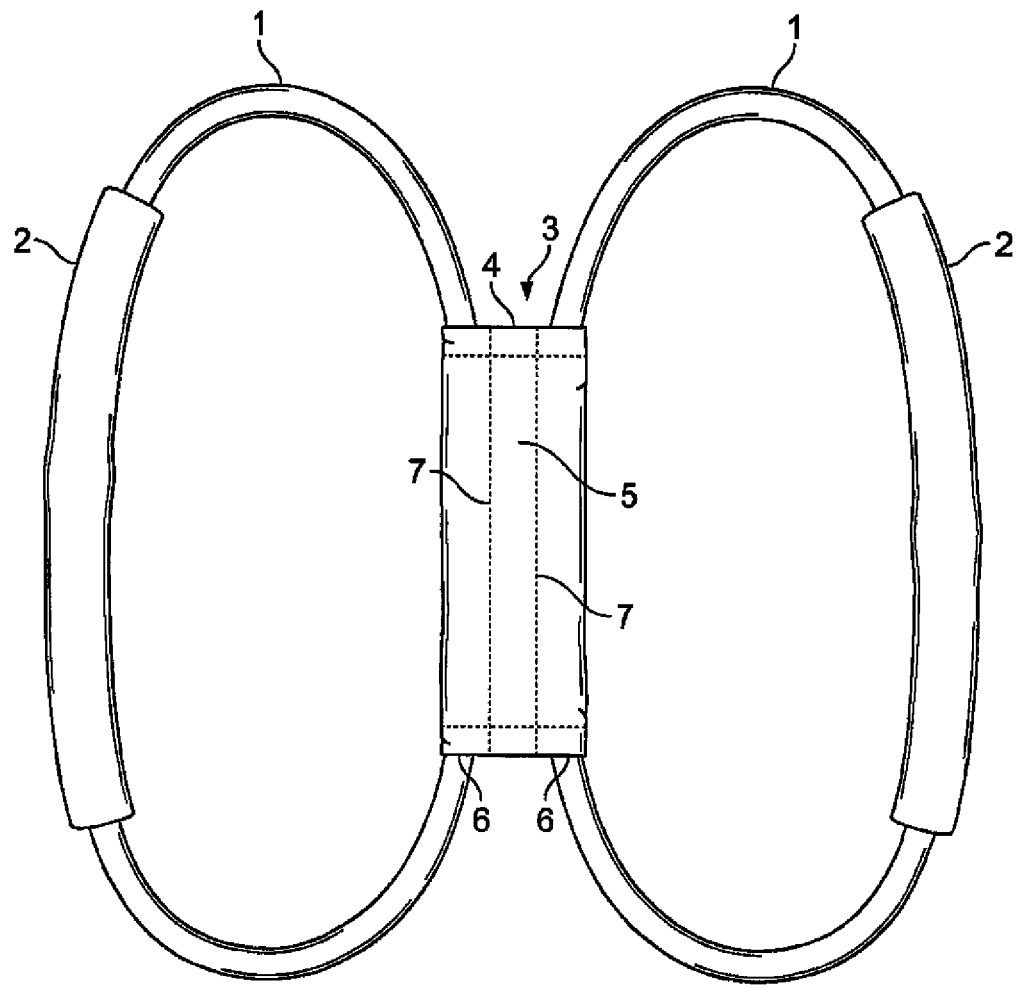
FIG. 3 is a front view of the device not on a user (showing resistance tubes contracted).

FIG. 3 is a basic view of the device according to one embodiment of the present invention. The device has a pair of closed loop resistance tubes 1 and a central harness member 3.

As shown in FIG. 7, the central harness member 3 preferably has a middle panel 5 and two side sleeves 6, separated by stitching lines 7 defining the side sleeves and separating them from the middle panel (where an anti-torsion member 4 may be contained, as described below). The harness 3 is preferably made with a soft or solid durable material, and may be provided in any shape (e.g. rectangle, triangle, polygon, square, circle or other shape). One function of the harness 3 is to serve as a spacer preventing interference between the loops 1. The central harness member 3 preferably is a sewn fabric sleeve for comfort (e.g. nylon, canvas, or any other durable fabric or fabric blend) but other embodiments are possible. A fabric harness may be particularly preferred for its light weight, and non-irritating construction. Unlike plastic components, the fabric harness does not create a sweaty or sticking area on the user's back, but may be capable of breathing and/or wicking moisture. In certain embodiments, the harness 3 may also be constructed so as to allow the user to open a front or back panel (or one or both side sleeves separately) to allow removal or swapping of resistance tubes (e.g. to insert tubes of a different size or resistance or multiple tubes). In this construction (not shown), the closure may be fastened by hook and loop strips, snaps or other fastening devices known in the art.

The harness may also be provided with frictional surfacing/texturing/coating to prevent creep, and/or may be provided with additional padding for comfort.

Each of the closed loop resistance tubes 1 is slidably received in a side sleeve 6 of the central harness member 3, which positions the two closed loop resistance tubes 1 roughly in the form of a figure "8". The closed loop resistance tubes 1 may be formed by attaching a length of rubber cord to itself to form a loop or "0". Alternatively, each loop may be a continuous circle of cord. The closed loop resistance tubes 1 may be natural or synthetic rubber cords (or any elastic material capable of easily expanding and contracting while providing progressive resistance as the material is stretched). Although the loops are described here as "tubes", it will be appreciated that these may also be of solid material, and may have any suitable cross-sectional shape.

The closed loop resistance tubes 1 may vary in length according to size and tension needed. They may be as short as 12 inches or as long as 36 inches. The device may further comprise an adjustment for the length and tension of the bands.

A handle 2 may be mounted to each closed loop resistance tube 1. When the device is used as in stabilization mode, the handles function as shoulder/underarm cushions or pads. When the device is used in stretching/exercise mode, the handles can be gripped by the user. The handle 2 may be comprised of foam, rubber, or other comfortable material and may vary from 3 inches in length to 12 inches in length (other dimensions being possible). It may also be desirable in certain embodiments to provide a fixed (non-sliding) handle or another form of hand-grip (not necessarily tube- or sleeve-shaped) or cushioning member/pad.

A rigid anti-torsion member 4 (shown in FIG. 7) may be disposed within the middle panel 5 of the central harness member 3 to provide support for the user's back and resist twisting/creeping when being put on or worn. The rigid anti-torsion member 4 may be comprised of a durable plastic material in a rod shape, or another solid material that keeps the central harness from distorting or folding and keeps the device centred on the user's back when worn.

Figure 1:
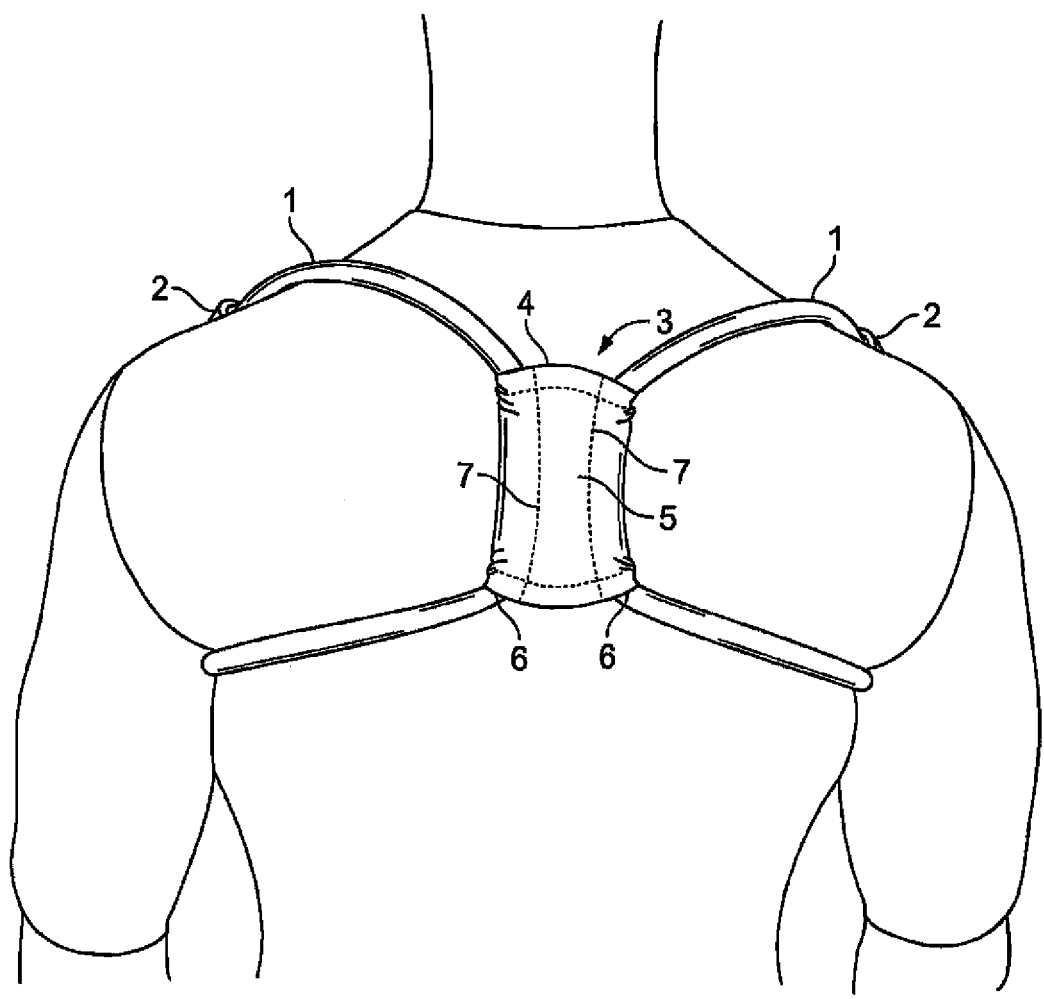
FIG. 1 is a front view of an embodiment of device in the stabilization mode.

FIG. 1 illustrates the device worn by a user. The device can be worn at any time a user would like to have proper posture. The user simply grasps each handle 2 in each hand, stretches the closed loop resistance tubes 1, inserts each arm in each tube, slides the tubes over the user's elbows and positions the handles 2 comfortably into place on the front of the user's shoulders and/or under the arms. The handles 2 provide a comfortable fit of the tubes 1 and prevent the resistance tubes from tugging on or bunching up the user's clothing or skin. In combination, the pair of closed loop resistance tubes 1 and central harness member 3 function to help the user keep their shoulders back and prevent forward rolling of the shoulders. Among other aspects, the rigid anti-torsion member 4 also functions to provide support to the upper vertebrae.

It will be appreciated that the device in the stabilization mode has a low profile and low degree of interference with user movements. It can be worn substantially "invisibly" under a user's jacket for an extended period while doing desk work, for example. In the stabilization mode, the device is worn and put on like a vest. Once demonstrated or illustrated (e.g. from package instructions), the function is simple for users to understand and does not require elaborate reaching or closures to put on or take off. Further, the user does not experience a feeling of being confined or bound, although the device provides an awareness of the user's posture and a gentle resistance against forward slump of the shoulders. Gradually with use, this awareness retrains the user, making him/her aware of posture even when not wearing or using the device.

Figure 2:
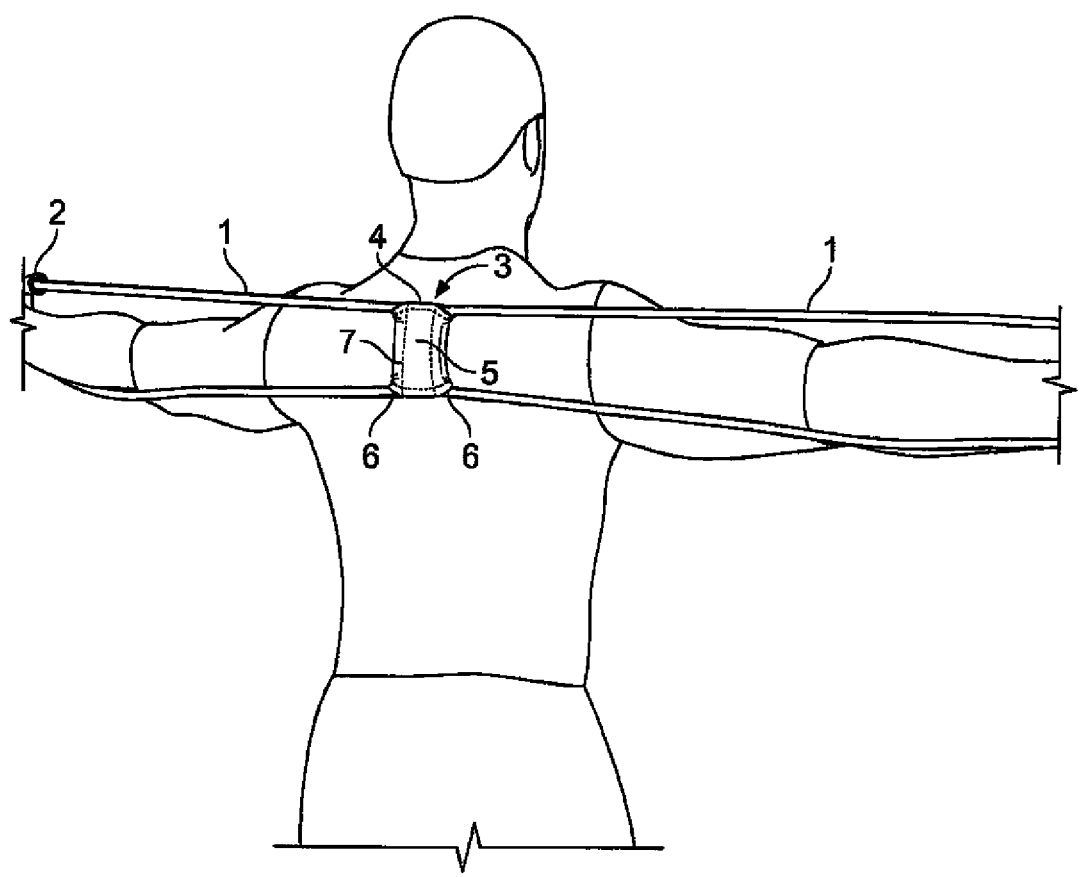
FIG. 2 is a front view of the device of FIG. 1 in the stretching/strengthening mode (with resistance tubes extended/enlarged).

FIG. 2 illustrates the device in use by a user in stretching/strengthening mode. For use as a stretching device, in general, a user grasps the handles and moves the device into a position as to be desired as to stretch each individual muscle group. A stretching program will typically include stretches for the pecs, shoulders, biceps, triceps or back. For use as an exercise device, a user grasps a handle in each hand and moves the handles as to make each individual muscle group to work in the form of exercise. A user will typically perform exercises for the chest, triceps, biceps, shoulders, or back.

This device assists to promote good posture and improves poor posture by retraining the shoulder complex how to maintain a neutral posture; lengthening overly tight muscles; strengthening overly weak muscles; and providing a support and stabilizer for the shoulder complex.

Figure 4A:
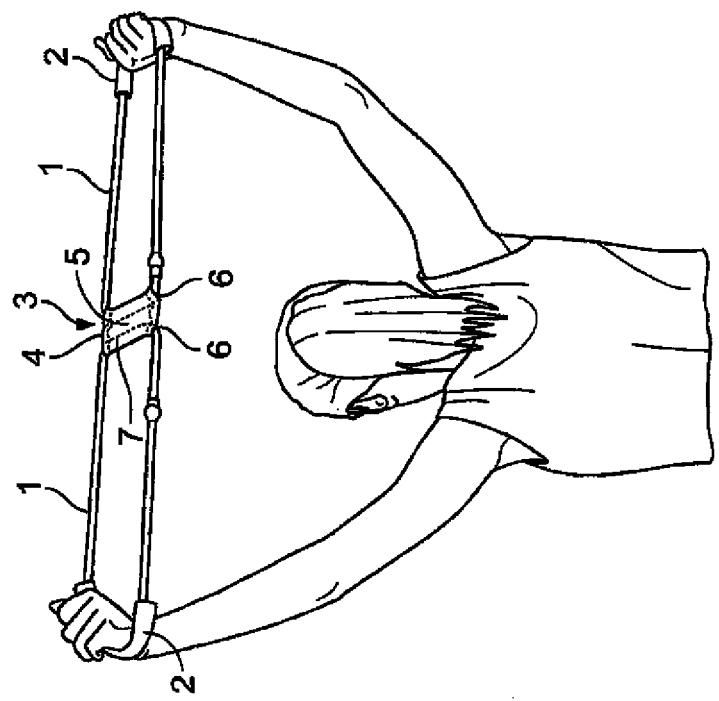
FIGS. 4A-4B show an embodiment of a chest stretch motion, using the device in stretching/strengthening mode.
Figure 4B:
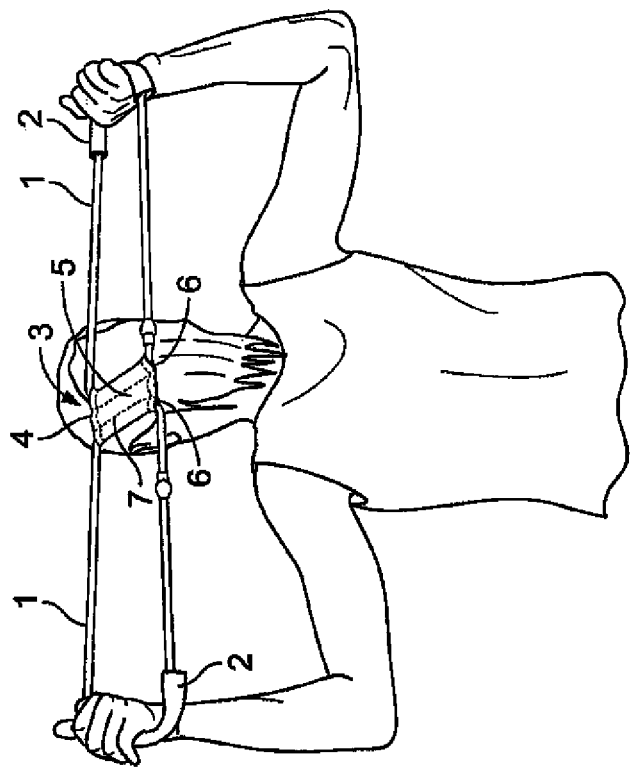
Figure 5C:
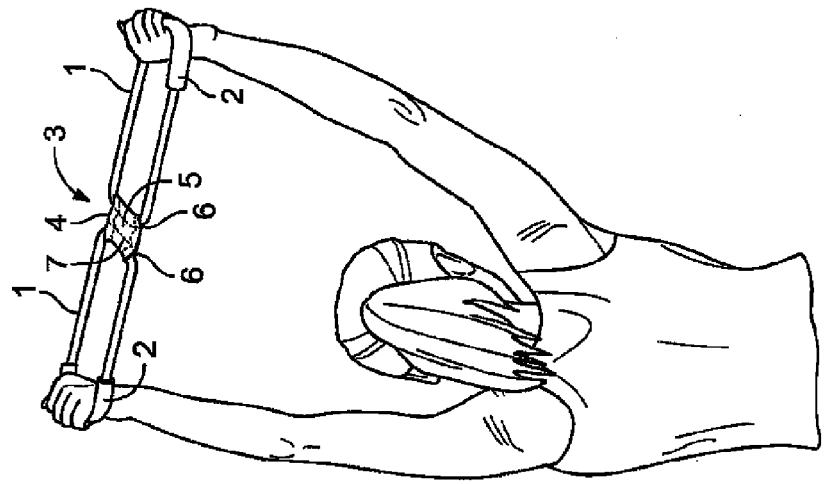
FIGS. 5A-5C show an embodiment of a lat stretch motion, using the device in stretching/strengthening mode.
Figure 5B:
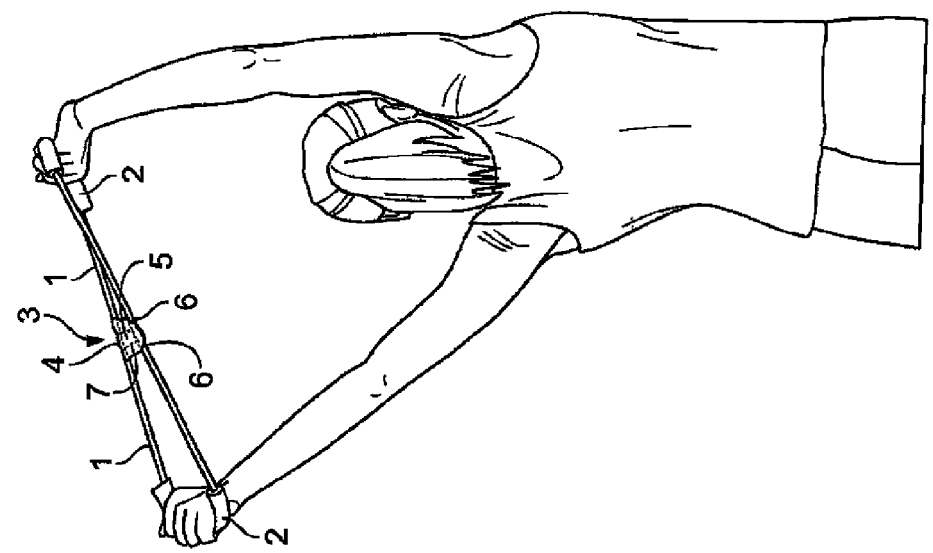
Figure 5A:
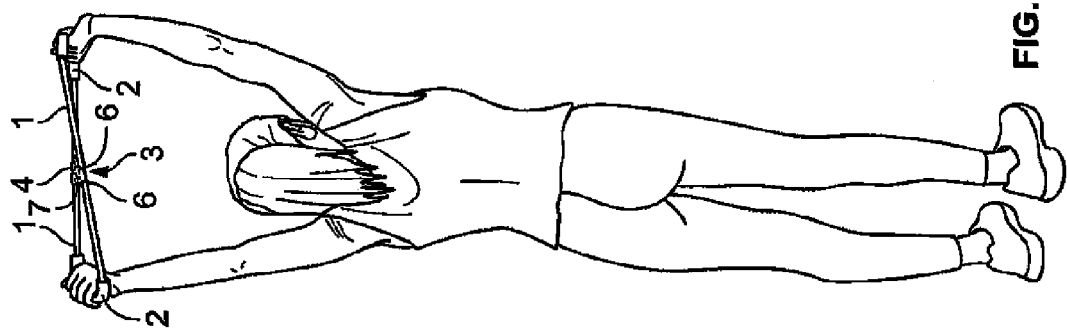

Some examples of the possible stretches/exercises are shown in FIGS. 4A-6B. In FIGS. 4A-4B, two forms of chest stretch are shown. In FIG. 5A, an overhead lat stretch is shown. As shown in FIGS. 5B, 5C, the device may be held overhead in extended form, and the user may lean side-to-side to lengthen and stretch lat and side muscles. In FIGS. 6A-6B, a shoulder stretch is illustrated. Since having strong and limber chest, lat and shoulder muscles is key for posture, the device's stretching/strengthening mode also serves the posture correction/therapeutic end. When tired, the device can be worn to prolong the effect of the stretching/strengthening and maintain good posture.

In stabilization mode, the user may also perform stretches on a smaller scale (e.g. by shrugging the shoulders, or rolling them forward against resistance). It will also be appreciated that the movements may be coupled with other body actions and may be part of a larger program of aerobic-type, core-strengthening type, or yoga type activity (just to take a few examples). The device may also be worn while exercising (e.g. to obtain a better stance while doing weight-training or running).

The scope of the claims should not be limited by the preferred embodiments set forth in the examples, but should be given the broadest purposive construction consistent with the description as a whole.

What is claimed is:

1. A dynamic stretching, strengthening and stabilization device for postural correction and retraining in a user, comprising:
    a central harness member having a middle panel, a first side sleeve, and a second side sleeve;
    a first closed loop resistance tube comprising a closed loop length, a portion of the closed loop length being located within the first side sleeve of the central harness member;
    a second closed loop resistance tube comprising a second closed loop length, a portion of the second closed loop length being located within the second side sleeve of the central harness member;
    a handle disposed along a length of each closed loop;
    wherein the user:
        can grip the handles and pull in opposing directions to actively engage the resistance tubes in a stretching/strengthening mode; and
        can position each closed loop over one of the user's arms so that the central harness member is positioned against the user's back while each of the first and second closed loops extends around the user's anterior pectoral and underarm region with the handles positioned to cushion where each closed loop engages the user's anterior pectoral or underarm region in a stabilization mode; each loop being sized to fit around the user's anterior pectoral or underarm region and provide passive resistance against forward shoulder curvature in the stabilization mode.

2. The device of claim 1 further comprising a rigid anti-torsion member disposed within the middle panel of the central harness member.

3. The device of claim 1, wherein the central harness member is fabric.

4. The device of claim 1, wherein the central harness member has a slide-resistant surface.

5. The device of claim 1, wherein the central harness member is sized to sit between the user's shoulder blades and the central harness member avoids creeping upward.

6. The device of claim 1, wherein the loops are disposed in the central harness member such that the loops do not touch or interfere with each other.

7. The device of claim 1, wherein each handle is between 3 inches to 12 inches in length.

8. The device of claim 1, wherein each closed loop resistance tube is between 12 to 36 inches in circumference.

9. The device of claim 1, further comprising a length adjustment for the closed loop resistance tubes.

10. The device of claim 1, further comprising a tension adjustment for the closed loop resistance tubes.

11. The device of claim 1, wherein the device is packaged with instructions for carrying out stretching or exercising movements in the stretching/strengthening mode.

12. The device of claim 1 wherein the handles are flexible and tubular.

13. The device of claim 1 wherein each closed loop is slidable within its respective sleeve, and each handle is slidable along its respective loop.

14. The device of claim 1 wherein, with the device positioned with each loop over one of the user's arms, a longitudinal axis of each handle is substantially aligned with a longitudinal axis of a side sleeve.

15. The device of claim 1 wherein, with the device positioned with each loop over one of the user's arms, a longitudinal axis of each of the side sleeves is substantially aligned with a longitudinal axis of the user.

16. The device of claim 1 wherein the device includes loops consisting of the two loops, and the device includes a harness consisting of the one harness.

17. The device of claim 1 wherein each handle extends along a length of each loop.

18. A method of using a dynamic stretching, strengthening and stabilization device for postural correction and retraining in a user, the device having:
   a central harness member having a middle panel, a first side sleeve, and a second side sleeve;
   a first of closed loop resistance tube comprising a closed loop length, a portion of the closed loop length being located within the first side sleeve of the central harness member;
   a second closed loop resistance tube comprising a second closed loop length, a portion of the second closed loop length being located within the second side sleeve of the central harness member;
   a handle disposed along a length of each closed loop;
   the method comprising the user:
      positioning each loop over one of the user's arms so that the central harness member is positioned against the user's back while each of the first and second closed loop extends around the user's anterior pectoral and underarm region with the handles positioned to cushion where each loop engages the user's anterior pectoral or underarm region in a stabilization mode; each loop being sized to fit around the user's anterior pectoral or underarm region and provide passive resistance against forward shoulder curvature in the stabilization mode.

19. The method of claim 18, further comprising removing the device from the stabilization mode to a stretching/strengthening mode by gripping the handles, extending the handles outward from the user's body to stretch and elastically enlarge the loops, and removing the loops from the user's arms while the loops are enlarged.

20. The method of claim 19, wherein the stretching/strengthening mode comprises extending the arms outward with the device disposed over the user's head in a lat stretch motion.

21. The method of claim 19, further comprising leaning the head to alternate sides while the arms are extended outward.

22. The method of claim 19, wherein the stretching/strengthening mode comprises extending the arms outward with the device disposed behind the user's body in a shoulder stretch motion.

23. The method of claim 19, wherein the stretching/strengthening mode comprises extending the arms outward with the device disposed in front of the user's body in a first chest stretch motion.

24. The method of claim 19, wherein the stretching/strengthening mode comprises extending the arms outward with the device disposed behind the user's head in a second chest stretch motion.

25. The method of claim 18, further comprising smoothly transitioning from the stabilization mode to a stretching/strengthening mode by gripping the handles, extending the handles outward from the user's body to stretch and elastically enlarge the loops, and removing the loops from the user's arms while the loops are enlarged, thereby freeing the device to permit exercising or stretching with the device in front of or behind the user.

* * * * *